United States Patent [19]

Wagle et al.

[11] Patent Number: 5,334,395

[45] Date of Patent: Aug. 2, 1994

[54] METHOD OF TREATING AN EPSTEIN-BARR VIRAL INFECTION

[75] Inventors: Sudhakar S. Wagle, Mequon, Wis.; Thomas Steinbach, Houston, Tex.; Carl H. Lawyer, Mequon, Wis.; William J. Hermann, Jr., Sealy, Tex.; Ali A. S. Gawish, Mequon, Wis.

[73] Assignee: Kremers-Urban Company, Milwaukee, Wis.

[21] Appl. No.: 934,554

[22] Filed: Aug. 24, 1992

Related U.S. Application Data

[63] Continuation-in-part of Ser. No. 803,844, Dec. 4, 1991, which is a continuation of Ser. No. 728,267, Jul. 11, 1991, abandoned, which is a continuation of Ser. No. 228,364, Aug. 4, 1988, Pat. No. 5,055,296, said Ser. No. 934,554, and a continuation of Ser. No. 780,084, is a continuation-in-part of Ser. No. 728,267, Jul. 11, 1991, abandoned, which is a continuation-in-part of Ser. No. 228,364, Aug. 4, 1988, Pat. No. 5,055,296.

[51] Int. Cl.$^5$ .......................................... A61K 35/407
[52] U.S. Cl. ..................................... 424/553; 514/21; 514/885; 530/846
[58] Field of Search ............... 424/553; 514/21, 885; 530/846

[56] References Cited

U.S. PATENT DOCUMENTS

| | | | |
|---|---|---|---|
| 3,778,510 | 12/1973 | Blonde | 424/553 |
| 4,148,788 | 4/1979 | Wang | 530/324 |
| 4,420,398 | 12/1983 | Castino | 210/641 |
| 4,426,324 | 1/1984 | Meienhofer | 530/301 |
| 4,428,938 | 1/1984 | Kisfaludy | 514/17 |
| 4,464,355 | 8/1984 | Fabricius | 424/85.2 |
| 4,468,379 | 8/1984 | Gottlieb | 424/534 |
| 4,537,878 | 8/1985 | Plotnikoff | 514/2 |
| 4,595,588 | 6/1986 | Baron | 424/89 |
| 4,595,780 | 6/1986 | Ogata | 564/79 |
| 4,596,798 | 6/1986 | Shipman, Jr. | 514/183 |
| 4,598,095 | 7/1986 | Nishimura | 514/632 |
| 4,602,037 | 7/1986 | Seborm | 514/512 |
| 4,603,122 | 7/1986 | Blough | 514/23 |
| 4,603,219 | 7/1986 | Verheyden | 560/255 |
| 4,604,404 | 8/1986 | Munson, Jr. | 514/494 |
| 4,605,658 | 8/1986 | Holy | 514/261 |
| 4,605,659 | 8/1986 | Verheyden | 514/262 |
| 4,606,917 | 8/1986 | Eppstein | 424/85.6 |
| 4,609,661 | 9/1986 | Verheyden | 514/262 |
| 4,609,662 | 9/1986 | Krenitsky | 514/262 |
| 4,612,314 | 9/1986 | Verheyden | 514/261 |
| 4,614,651 | 9/1986 | Jarvis, Jr. | 424/85.4 |
| 4,614,731 | 9/1986 | Horecker | 514/12 |
| 4,617,304 | 10/1986 | Ashton | 514/261 |
| 4,621,140 | 11/1986 | Verheyden | 544/276 |
| 4,622,430 | 11/1986 | Dekker | 564/458 |
| 4,625,026 | 11/1986 | Kim | 544/249 |
| 4,626,524 | 12/1986 | Server | 514/13 |
| 4,628,063 | 12/1986 | Haines | 514/626 |
| 4,629,811 | 12/1986 | Dominianni | 564/99 |
| 4,631,149 | 12/1986 | Rinehart, Jr. | 540/546 |
| 4,644,055 | 2/1987 | Kettner | 530/330 |
| 4,668,660 | 5/1987 | Paessens | 514/383 |
| 4,670,437 | 6/1987 | Abdulla | 514/247 |
| 4,699,898 | 10/1987 | Gottlieb | 514/18 |
| 4,708,818 | 11/1987 | Montagnier | 435/5 |
| 4,710,380 | 12/1987 | Gottlieb | 424/534 |

FOREIGN PATENT DOCUMENTS

| | | |
|---|---|---|
| 0140134 | 5/1985 | European Pat. Off. |
| 0250234 | 12/1987 | European Pat. Off. |
| 357958 | 3/1990 | European Pat. Off. |

OTHER PUBLICATIONS

Andrews et al., *JAMA*, 146, 1107 (1951).
Barksdale, *South. Med. Jour.*, 50, 1524 (1957).
Barksdale, et al., *Virginia Medical Monthly*, 81, 321 (1954).
Barrock, *Medical Times*, 1, (Aug. 1958).
Boreen, *Minnesota Medicine*, 25, 276 (1942).
Burks, Jr. *Journal of the Louisiana Medical Society*, 106, 92 (1954).
Burks, Jr. and Knox *Archives of Dermatology and Syphilology*, 70 508 (1954).
Center for Disease Control, Dept. Health and Human Services, Chronic *Fatigue Syndrome*, Mar. 22, 1988.
Chase, *Wall Street Journal*, Apr. 28, 1988, at 14, at col. 1.
Gaskell, *Brit. Med. J.*, 1037 (Jun. 11, 1949).
Gathings, *Am. J. Surgery*, 88, 429 (1954).
Gladner, *Ann. N.Y. Aca. Sci* 47.
Harris, et al., *Oral Surgery*, 7, 239 (1954).
Hellinger, et al., *JAMA*, 260, 971 (Aug. 19, 1988).
Heywood, *Clinical Medicine*, 3, 425 (1956).
Hjerten, *Archives of Biochemistry and Biophysics*, Suppl. 1, 147 (1962).
Hjertsen and Mosbach, *Analytical Biochemistry*, 3, 109 (1962).
Holtman, *Oral Surgery*, 7, 12 (1954).
Judge, *Proc. Soc. Exptl. Biol. Med.*, 123, 199 (1966).
Kozelka and Marshall, *Clinical Medicine*, 3, 245 (1956).
Kutapressin-Drug Package Insert, Kremers-Urban.
Li, et al., *Nature*, 219, 1163 (Sep. 14, 1968).

(List continued on next page.)

Primary Examiner—Douglas W. Robinson
Assistant Examiner—Jean C. Witz
Attorney, Agent, or Firm—Tilton, Fallon, Lungmus & Chestnut

[57] ABSTRACT

A therapeutic method for treating Epstein-Barr virus infection. The method comprises administering a therapeutically-effective amount of a mammalian liver extract, the extract being characterized by being heat stable, insoluble in acetone and soluble in water, peptide or peptide fragment selected from the groups consisting of Sequence Identification Numbers 1-9.

4 Claims, 7 Drawing Sheets

OTHER PUBLICATIONS

Li, et al., *Proc. Soc. Exptl. Biol. Med.,* 114, 504 (1963).
Li, et al., *Proc. Soc. Exptl. Biol. Med.,* 109, 534 (1962).
Li, et al., *J. Nat'l Cancer Inst.,* 41, 1249 (Nov. 1968).
Li, et al., *Ann. N.Y. Acad. Sci.,* 130, 374 (1965).
Lichtenstein and Stillians, Arch. Dermatology and Syphilology, 45, 595 (1942).
Lubowe, *Clinical Medicine,* 59, 8 (1952).
Marshall, et al., *Am. J. Surgery,* 90, 47 (1955).
Marshall, Maryland State Med. J., (Jun. 1960).
Marshall, *Am. J. Surgery,* 84(6), 675 (1952).
Marshall, and Schadeberg, *Wisconsin Medical Journal,* 49, 369 (1950).
Marshall and Schadeberg, *Indian J. Veneral Diseases,* 16, 89 (1950).
Marshall, *J.M.A. Alabama,* 13, 255 (1944).
Marshall, *Mississippi Valley Med. J.,* 61, 172 (1939).
Marshall, *Med. World,* 57, 101 (1939).
Marshall, *Northwest Medicine,* 38, 467 (1939).
Marshall, *J. Invest. Derm.,* 2, 105 (1939).
Marshall, *A. J. Surgery,* 448 (Oct. 1951).
Marshall, *Medical Times,* 70, 222 (1951).
Marshall, *Indian J. Veneral Diseases and Dermatology,* 20, 99 (1954).
Marshall, *The Journal–Lancet,* 60, 117 (1940).
Marshall, *Minnesota Medicien,* 25, 796 (1942).
Marshall, *Arizona Medicine,* 14(1), 11 (1957).
Marshall, *Mississippi Valley Med. J.,* 76, 199 (1954).
Mitchell-Heggs, *Brit. Med. J.,* 2, 1079 (1951).
Montefiori, et al., *J. Clin. Micro.,* 26, 231 (Feb. 1988).
Montefiori and Mitchell, *Proc. Nat'l Acad. Sci. U.S.A.,* 84(9), 2985 (May 1987).
Nierman, *Journal of the Indiana State Medical Association,* 45, 497 (1952).
Osbahr, et al., *Biochim. Biophys. Acta.* 86, 535 (1964).
Pensky and Goldberg, *The Journal–Lancet,* 75(11), 490 (Nov. 1955).
Pensky and Goldberg, *New York State Journal of Medicine,* 53, 2238 (1953).
*Pharmacopeia of the United States,* 15, 379.
Pollner, *Medical World News,* 35 (Jun. 13, 1988).
Poole, *South Med. J.,* 50, 207 (1957).
Ruggieri, *Science,* 194, 491 (1976)
Schmeer and Huala, *Ann. N.Y. Acad. Sci.,* 118, 605 (1965).
Schmeer, *Science,* 144, 413 (1964).
Smith, *HIV and Other Highly Pathogenic Viruses,* Academic Press, Inc. (1988)
Stillians, *Mississippi Valley Medical Journal,* 64, 135 (1942).
Stokes and Sternberg, *Archives of Dermatology and Syphilology,* 40, 345 (1939).
Sutton, *Archives of Dermatology and Syphilology,* 18, 887 (1928).
Tewksbury and Stahmann, *Arch. Biochem. Biophys.* (U.S.), 112, 453 (1965).
Tewksbury, *Archives Int'l de Pharmacodynamic et de Therapie,* 173, 426 (1968).
Tewksbury, *Dissertation Absttracts International–Part II,* 25–04, 2214 (1964).
Walters, *Ohio State Medical Journal,* 44, 697 (1948).
van der Horst, et al., "Lack of Effect of Peroral Acyclovir for the Treatment of Acute Infectious Mononucleosis", *The Journal of Infectious Diseases,* 1991; 164:788–92.

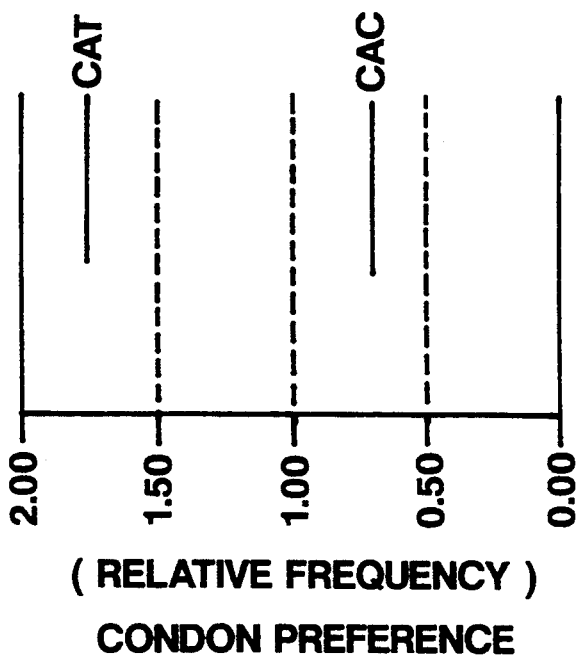
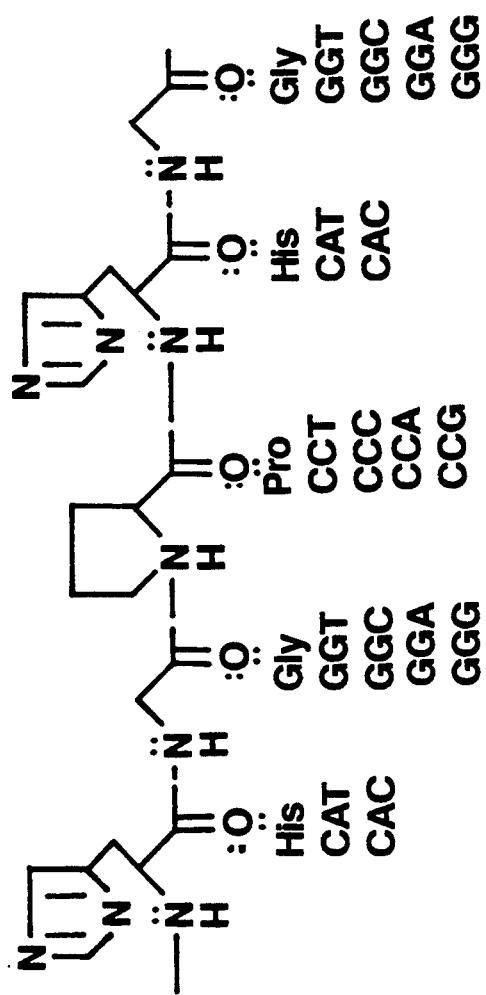
Fig. 1

Fig. 2a

KU214 and 215 peptide:
5'GGGCCGCATGGGCAAAGTATTATGCTCGGCCTGAACAGTGTATTTATCCAAGTCAATAATACGTCAAGCTGCACCTTTT
3'CCCGGCGTACCCGTTTCATAATACGAGCCGGACTTGTCACATAAATAGGTTCAGTTCACGTTATTATGCAGTTCGACGTGGAAAA TTTGACTTCTGCTGG    CTATAAATGTGCATTTATCAGAAGTGATGTAAACACTATTCTAGTACTGTTCCTTCATCTAGA
AAACTGAAGACGACC...GATATTTACACGTAAATAGTCTTCAACTACATTGTGATAAGATCATGACAAGGAAGTAGATCT TTGATCAATTTAATTAAAATTAAGCACTAAAAAAAAAA    CTATCGATTCTGGAACCTTCAGAGG3'
AACTAGTTAAATTAATTTTAATTCGTGATTTTTTTTTTT...GATAGCTAAGACCTTGGAAGTCTCC5'

5'CATGGICCICATGGI3' PRIMER#1

5'CCTCTGAAGGTTCCAGAATCGATAG3' PRIMER#2  (CLONTECH UNI-AMP PRIMER)

Cycle 1   ↓denature. re-anneal

5'GGGCCGCATGGGCAAAGTATTATGCTCGGCCTGAACAGTGTATTTATCCAAGTGCAATAATACGTCAAGCTGCACCTTT
TTTGACTTCTGCTGG...CTATAAATGTGCATTTATCAGAAGTGATGTAAACACTATTCTAGTACTGTTCCTTCATCTAG
ATTGATCAATTTAATTAAAATTAAGCACTAAAAAAAAAAAAAA...CTATCGATTCTGGAACCTTCAGAGG3'

PRIMER#2 EXTENDS <-------------3'GATAGCTAAGACCTTGGAAGTCTCC5'

5'CATGGICCICATGGI3' PRIMER#1--------------> EXTENDS
    ..........
3'   CCCGGCGTACCCGTTTCATAATACGAGCCGGACTTGTCACATAAATAGGTTCACGTTATTATGCAGTTCGACGTGG
AAAAAACTGAAGACGACCGATATTTACACGTAAATAGTCTTCAACTACATTGTGATAAGATCATGACAAGGAAGTAGATC
TAACTAGTTAAATTAATTTTAATTCGTGATTTTTTTTTTTTTGATAGCTAAGACCTTGGAAGTCTCC5'

Fig. 2b

Cycle 1 ↓ Polymerase, dNTPs

```
5'GGGCCGCATGGGCAAAGTATTATGCTCGGCCTGAACAGTGTATTTATCCAAGTGCAATAATACGTCAAGCTGCACCTTTT
3'CCCGGCGTACCCGTTTCATAATACGAGCCGGACTTGTCACATAAATAGGTTCACGTTATGCAGTTCGACGTGGAAAA

TTTGACTTCTGCTGG    CTATAAATGTGCATTTATCAGAAGTGTAAACACTATTCTAGTACTGTTCCTTCATCTAGA
AAACTGAAGACGACC...GATATTTACACGTAAATAGTCTTCAACTACATTTGTGATAAGATCATGACAAGGAAGTAGATCT

TTGATCAATTTTAATTAAAATTAAGCACTAAAAAAAAAAA     CTATCGATTCTGGAACCTTCAGAGG3'
AACTAGTTAAAATTAATTTTAATTCGTGATTTTTTTTTTTT...GATAGCTAAGACCTTGGAAGTCTCC5'
```

Cycle 2 ↓ denature, re-anneal

```
5'GGGCCGCATGGGCAAAGTATTATGCTCGGCCTGAACAGTGTATTTATCCAAGTGCAATAATACGTCAAGCTGCACCTTTT
3'CCCGGCGTACCCGTTTCATAATACGAGCCGGACTTGTCACATAAATAGGTTCACGTTATGCAGTTCGACGTGGAAAA

TTTGACTTCTGCTGG    CTATAAATGTGCATTTATCAGAAGTGTAAACACTATTCTAGTACTGTTCCTTCATCTAGA
AAACTGAAGACGACC...GATATTTACACGTAAATAGTCTTCAACTACATTTGTGATAAGATCATGACAAGGAAGTAGATCT

TTGATCAATTTTAATTAAAATTAAGCACTAAAAAAAAAAA     CTATCGATTCTGGAACCTTCAGAGG3'
AACTAGTTAAAATTAATTTTAATTCGTGATTTTTTTTTTTT...GATAGCTAAGACCTTGGAAGTCTCC5'
```

```
5'GGGCCGCATGGGCAAAGTATTATGCTCGGCCTGAACAGTGTATTTATCCAAGTGCAATAATACGTCAAGCTGCACCTTT
TTTGACTTCTGCTGG...CTATAAATGTGCATTTATCAGAAGTAAACACTATTCTAGTACTGTTCCTTCATCTAG
ATTGATCAATTTTAATTAAAATTAAGCACTAAAAAAAAAAA...CTATCGATTCTGGAACCTTCAGAGG3'
                PRIMER#2 EXTENDS<----------3'GATAGCTAAGACCTTGGAAGTCTCC5'
        PRIMER#1------------->EXTENDS
5'CATGGICCICATGGI3'
```

Fig. 2c

3'  . . . . . . . . . .
CCGGGCGTACCCGTTTCATAATACGAGCCGGACTTGTCACATAAAATAGGTTCACGTTATTATGCAGTTCGACGTGG
AAAAAACTGAAGACGACCGATATTTACACGTCTAAATAGTCTTCAACTACATTGTGATAAGATCATGACAAGAAGTAGATC
TAACTAGTTAAAATTAATTTAATTCGTGATTTTTTTTTTTTTGATAGCTAAGACCTTGGAAGTCTCC5'
5'GGCCCGCATGGGCAAAGTATTATGCTCGGCCTGAACAGTGTATTTATCCAAGTGCAATAATACGTCAAGCTGCAACCTTT
TATTTTATCCAAGTGCAATATACGTCAATATACGTCAAGCTGCAATATACGTCAAGGAAGTCTCC5'

TTTGACTTCTGCTGG...CTATAAATGTGCATTTATCAGAAGTTGATGTAAACACTATTCTAGTACTGTTCCTTCATCTAG
ATTGATCAATTTTAATTAAAATTAAGCACTAAAAAAAAAAAA...CTATCGATTCTGGAACCTTCAGAGG3'
. . . . . . . . . .
PRIMER#2 EXTENDS<--------------3'GATAGCTAAGACCTTGGAAGTCTCC5'
5'CATGGICCICATGGI3' PRIMER#1----------->EXTENDS
. . . . . . . . . .
3' . . . . . . . . . .
CCGGGCGTACCCGTTTCATAATACGAGCCGGACTTGTCACATAAAATAGGTTCACGTTATTATGCAGTTCGACGTGG
AAAAAACTGAAGACGACCGATATTTACACGTCTAAATAGTCTTCAACTACATTGTGATAAGATCATGACAAGAAGTAGATC
TAACTAGTTAAAATTAATTTAATTCGTGATTTTTTTTTTTTTGATAGCTAAGACCTTGGAAGTCTCC5

↓ Cycle 2    Polymerase. dNTPs

5GGGCCCGCATGGGCAAAGTATTATGCTCGGCCTGAACAGTGTATTTATCCAAGTGCAATAATACGTCAAGCTGCACCTTTT
3CCCGGGCGTACCCGTTTCATAATACGAGCCGGACTTGTCACATAAATAGGTTCACGTTATTATGCAGTTCGACGTGGAAAA

TTTGACTTCTGCTGG    CTATAAATGTGCATTTATCAGAAGTTGATGTAAACACTATTCTAGTACTGTTCCTTCATCTAGA
AAACTGAAGACGACC    GATATTTACACGTAAATAGTCTTCAACTACATTTGTGATAAGATCATGACAAGGAAGATCT

TTGATCAATTTTAATTAAAATTAAGCACTAAAAAAAAAAAAAAA    CTATCGATTCTGGAACCTTCAGAGG3'
AACTAGTTAAAATTAATTTAATTCGTGATTTTTTTTTTTTTT...GATAGCTAAGACCTTGGAAGTCTCC5'

Fig. 2d

5'GGGCCCGCATGGGCAAAGTATTATGCTCTCGGCCTGAACAGTGTATTTTATCCAAGTGCAATAATACGTCAAGCTGCACCTTTT
3'CCCGGGCGTACCCGTTTCATAATACGAGACGACC...GATATTTACACGTAAATAGTCTTCAACTACATTGTGATAAGATCATGACAAGGAAGTAGATCT

TTTGACTTCTGCTGG                                       CTATCGATTCTGGAACCTTCAGAGG3'
AAACTGAAGACGACC                                       GATAGCTAAGACCTTGGAAGTCTCC5'

TTGATCAATTTTAATTAAAATTAAGCACTAAAAAAAAAAAAAAAA
AACTAGTTAAAATTAATTTTAATTCGTGATTTTTTTTTTTTTT

5'GGGCCCGCATGGGCAAAGTATTATGCTCTCGGCCTGAACAGTGTATTTTATCCAAGTGCAATAATACGTCAAGCTGCACCTTTT
3'CCCGGGCGTACCCGTTTCATAATACGAGACGGACTTGTCACGTTATTATGCAGTTCGACGTGGAAAA

TTTGACTTCTGCTGG                                       CTATCGATTCTGGAACCTTCAGAGG3'
AAACTGAAGACGACC                                       GATAGCTAAGACCTTGGAAGTCTCC5'

TTGATCAATTTTAATTAAAATTAAGCACTAAAAAAAAAAAAAAAA
AACTAGTTAAAATTAATTTTAATTCGTGATTTTTTTTTTTTTT

5'GGGCCCGCATGGGCAAAGTATTATGCTCTCGGCCTGAACAGTGTATTTTATCCAAGTGCAATAATACGTCAAGCTGCACCTTTT
3'CCCGGGCGTACCCGTTTCATAATACGAGACGGACTTGTCACGTTATTATGCAGTTCGACGTGGAAAA

TTTGACTTCTGCTGG                                       CTATCGATTCTGGAACCTTCAGAGG3'
AAACTGAAGACGACC                                       GATAGCTAAGACCTTGGAAGTCTCC5'

TTGATCAATTCTAAAATTAAAATTAAGCACTAAAAAAAAAAAAAAAA
AACTAGTTAAAATTAATTTTAATTCGTGATTTTTTTTTTTTTT
                        ↓
                   further Cycles

SEQUENCE LISTING ( 1 ) GENERAL INFORMATION:

(iii) NUMBER OF SEQUENCES: 9

(2) INFORMATION FOR SEQ ID NO:1:

(i) SEQUENCE CHARACTERISTICS:
        (A) LENGTH: 32 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:1:

```
Gly Pro His Gly Gln Ser Ile Met Leu Gly Leu Asn Ser Val Phe Tyr
 1               5                  10                  15
Pro Ser Ala Ile Ile Arg Gln Ala Ala Pro Phe Phe Asp Phe Cys Trp
            20                  25                  30
```

(2) INFORMATION FOR SEQ ID NO:2:

(i) SEQUENCE CHARACTERISTICS:
        (A) LENGTH: 96 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:2:

```
GGGCCGCATG GGCAAAGTAT TATGCTCGGC CTGAACAGTG TATTTTATCC AAGTGCAATA      60
ATACGTCAAG CTGCAGCTTT TTTTGACTTC TGCTGG                                96
```

(2) INFORMATION FOR SEQ ID NO:3:

(i) SEQUENCE CHARACTERISTICS:
        (A) LENGTH: 110 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:3:

```
CTATAAATGT GCATTTATCA GAAGTTGATG TAAACACTAT TCTAGTACTG TTCCTTCATC      60
TAGATTGATC AATTTTAATT AAAATTAAGC ACTAAAAAAA AAAAAAAAA                 110
```

(2) INFORMATION FOR SEQ ID NO:4:

(i) SEQUENCE CHARACTERISTICS:
        (A) LENGTH: 8 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:4:

```
Tyr Lys Cys Ala Phe Ile Arg Ser
 1               5
```

(2) INFORMATION FOR SEQ ID NO:5:

(i) SEQUENCE CHARACTERISTICS:
        (A) LENGTH: 25 base pairs
        (B) TYPE: nucleic acid
        (C) STRANDEDNESS: unknown
        (D) TOPOLOGY: unknown (ii) MOLECULE TYPE: DNA (genomic)

( x i ) SEQUENCE DESCRIPTION: SEQ ID NO:5:

CTATAAATGT GCATTTATCA GAAGT    25

( 2 ) INFORMATION FOR SEQ ID NO:6:

( i ) SEQUENCE CHARACTERISTICS:
    ( A ) LENGTH: 21 amino acids
    ( B ) TYPE: amino acid
    ( C ) STRANDEDNESS: unknown
    ( D ) TOPOLOGY: unknown ( i i ) MOLECULE TYPE: peptide ( x i ) SEQUENCE DESCRIPTION: SEQ ID NO:6:

```
Ile  Asn  Val  His  Leu  Ser  Glu  Val  Asp  Val  Asn  Thr  Ile  Leu  Val  Leu
1              5                   10                            15

Phe  Leu  His  Leu  Asp
              20
```

( 2 ) INFORMATION FOR SEQ ID NO:7:

( i ) SEQUENCE CHARACTERISTICS:
    ( A ) LENGTH: 65 base pairs
    ( B ) TYPE: nucleic acid
    ( C ) STRANDEDNESS: unknown
    ( D ) TOPOLOGY: unknown ( i i ) MOLECULE TYPE: DNA (genomic)

( x i ) SEQUENCE DESCRIPTION: SEQ ID NO:7:

CTATAAATGT GCATTTATCA GAAGTTGATG TAAACACTAT TCTAGTACTG TTCCTTCATC    60

TAGAT    65

( 2 ) INFORMATION FOR SEQ ID NO:8:

( i ) SEQUENCE CHARACTERISTICS:
    ( A ) LENGTH: 50 amino acids
    ( B ) TYPE: amino acid
    ( C ) STRANDEDNESS: unknown
    ( D ) TOPOLOGY: unknown ( i i ) MOLECULE TYPE: peptide ( x i ) SEQUENCE DESCRIPTION: SEQ ID NO:8:

```
Gly  Pro  His  Gly  Gln  Ser  Ile  Met  Leu  Gly  Leu  Asn  Ser  Val  Phe  Tyr
1              5                   10                            15

Pro  Ser  Ala  Ile  Ile  Arg  Gln  Ala  Ala  Pro  Phe  Phe  Asp  Phe  Cys  Trp
              20                   25                            30

Xaa  Xaa  Xaa  Xaa  Xaa  Xaa  Xaa  Xaa  Xaa  Xaa  Tyr  Lys  Cys  Ala  Phe  Ile
              35                   40                            45

Arg  Ser
     50
```

( 2 ) INFORMATION FOR SEQ ID NO:9:

( i ) SEQUENCE CHARACTERISTICS:
    ( A ) LENGTH: 63 amino acids
    ( B ) TYPE: amino acid
    ( C ) STRANDEDNESS: unknown
    ( D ) TOPOLOGY: unknown ( i i ) MOLECULE TYPE: peptide ( x i ) SEQUENCE DESCRIPTION: SEQ ID NO:9:

```
Gly  Pro  His  Gly  Gln  Ser  Ile  Met  Leu  Gly  Leu  Asn  Ser  Val  Phe  Tyr
1              5                   10                            15

Pro  Ser  Ala  Ile  Ile  Arg  Gln  Ala  Ala  Pro  Phe  Phe  Asp  Phe  Cys  Trp
```

```
              20                      25                          30
Xaa Xaa Xaa Xaa Xaa Xaa Xaa Xaa Xaa Xaa Ile Asn Val His Leu Ser
            35                  40              45

Glu Val Asp Val Asn Thr Ile Leu Val Leu Phe Leu His Leu Asp
            50              55                  60
```

METHOD OF TREATING AN EPSTEIN-BARR VIRAL INFECTION

This application is a continuation-in-part of U.S. Ser. No. 803,844 filed Dec. 4, 1991, pending, which in turn is a continuation in-part of U.S. Ser. No. 07/728,267 filed Jul. 11, 1991, abandoned, which is a continuation of U.S. Ser. No. 07/228,364 filed Aug. 4, 1988, now U.S. Pat. No 5,055,296. This application is also a continuation in-part of U.S. Ser. No. 07/780,084 filed Oct. 15, 1991, abandoned, which in turn is a continuation in-part of U.S. Ser. No. 07/728,267 filed Jul. 11, 1991, abandoned, which is a continuation of U.S. Ser. No. 07/228,364 filed Aug. 4, 1988, now U.S. Pat. No. 5,055,296.

BACKGROUND OF THE INVENTION

1. Field of the Invention

The present invention is directed to a method of treating Epstein-Barr virus infection and to the discovery that a mammalian liver extract that is efficacious in treating such diseases. The present invention is also directed to a method of treating such diseases with this same mammalian liver extract and/or with polypeptides shown in Sequence identification numbers 1-9.

2. Description of the Prior Art

Epstein-Barr virus is an oncogenic virus. This virus is known to cause mononucleosis, nasopharyngeal cancer, Burkitt's lymphoma, Hodgkin's disease and X-linked lymphoproliferation. Currently, Epstein-Barr virus infection is treated with Acyclovir. In order, however, to obtain anti-EBV viral activity a very high dosage to produce a concentration of 2.0 µg/ml must be given. This dosage, however, in humans is not effective, because Acyclovir often crystallizes in the kidneys at this dose.

Mammalian liver extract has been used for the treatment of a wide range of infectious and noninfectious dermatologic conditions, including ache vulgaris, *Journal Invest Dermatology*, 2:205-218 (1939); first and second degree burns, *Mississippi Valley Medical Journey*, 76:199 (1954); sunburn, *Clinical Medicine*, 3:245 (1956); poison ivy dermatitis, *Clin. Med.*, 3:425 (1956) and Herpes zoster, *Southern Medical Journal*, 50:1524 (1957). The active principle and mechanism have not been described. Although some medical practitioners have used liver extract for the treatment of dermatologic conditions, it is not regarded as an antiviral or immune modulator agent even for skin therapy.

Mammalian liver extract has been reported to have bradykinin potentiating activity. Tewksbury et al., *Arch. Blochem. Biophys. (U.S.)*, 112, 453 (1965); Tewksbury, *Archives Int'l. de Pharmacodynamie et de Therapie*, 173, 426 (1968); Tewksbury, *Dissertation Abstracts International-Part II*, Vol. 25/04, p. 2214 (1964). Further, one commercially-available liver extract (sold under the trademark KUTAPRESSIN by Kremers-Urban Co., Milwaukee, Wisconsin) exerts its action, according to product literature, only with respect to tissues that have been injured and when inflammation and edema are present.

In U.S. Pat. No. 5,055,296, the use of a heat stable acetone-insoluble, water-soluble mammalian liver extract was shown to be effective in the treatment of mammals infected with nondermatologic viruses, in particular, in the treatment of chronic fatigue syndrome. Thus, with this background, the inventors endeavored to discover a method to treat Epstein-Bart virus infection.

SUMMARY OF THE INVENTION

The present invention provides a method of treating Epstein-Barr virus infection involving administering to a mammal having said disease a therapeutically-effective amount of mammalian liver extract, the extract being characterized by being heat stable, insoluble in acetone and soluble in water. The terminology "heat stable" means that the liver extract does not lose appreciable activity at temperatures at about 100° C. in water over ten minutes. Additionally, this invention relates to a method of treating EBV vital infection involving administering to a mammal having said disease a therapeutically effective amount of a peptide or peptide fragment selected from the group consisting of Sequence Identification Nos. 1-9.

BRIEF DESCRIPTION OF THE DRAWINGS

FIG. 1 shows codon bias for His using all pig sequences in GENBANK 66.

FIGS. 2, 2a, 2b, 2c and 2d illustrate the strategy used for sequencing the active peptide.

DETAILED DESCRIPTION OF THE PRESENTLY PREFERRED EMBODIMENTS

Figure 3:
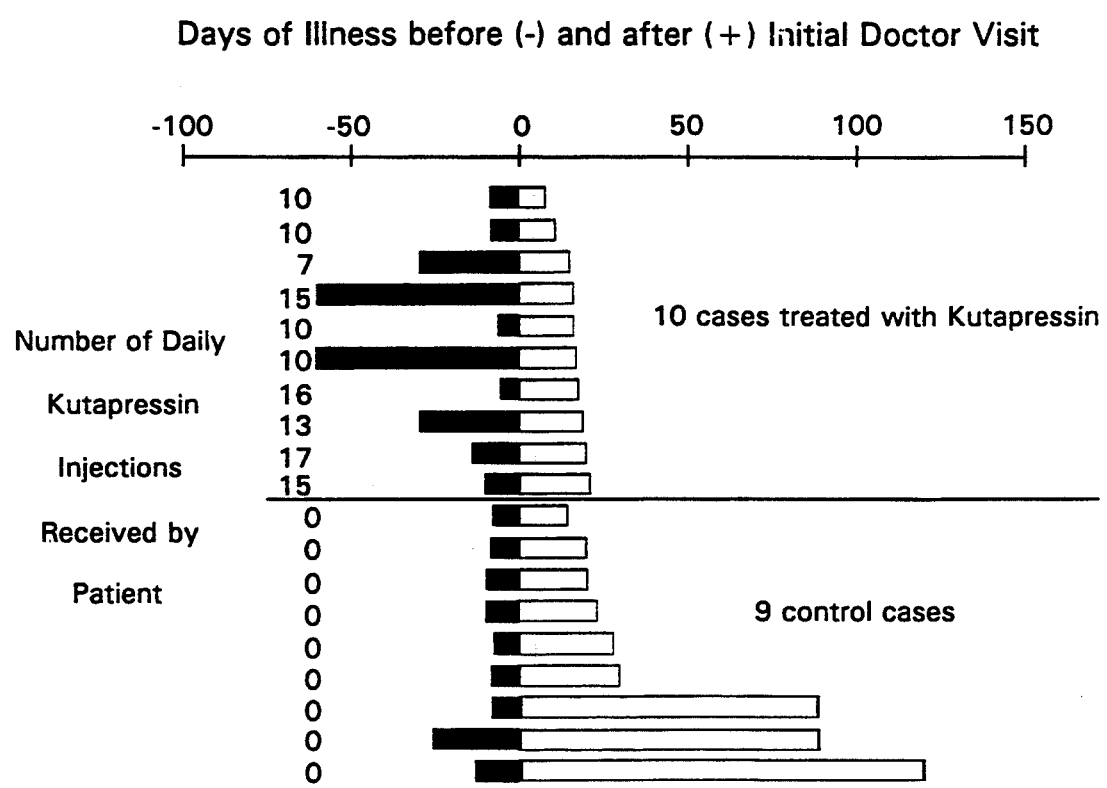
FIG. 3 shows number of daily KUTAPRESSIN (Kremers-Urban Company) injections received by patient versus days of illness with infectious mononucleosis.

The portion of mammalian liver extract that has been discovered to be effective in treating Epstein-Barr virus infection is the fraction which is heat stable, insoluble in acetone and soluble in water. The liver extract prepared according to the disclosure herein is free from fatty acids, and vitamins, and specifically is free from vitamin B-12, a vitamin naturally occurring in liver. Work in progress suggests polysaccharides may be present in KUTAPRESSIN (Kremers-Urban Co.) in the form of proteoglycans and/or glycoproteins. The same liver extract has been used heretofore in treating skin conditions.

Preparation of the Liver Extract

The liver extract employed in the present invention is prepared by separating a fraction from mammalian livers, preferably porcine liver. The starting material may be a liver preparation as described in *Pharmacopeia of the United States*, Vol. 15, p. 379 (which describes a boiled liver extract suitable for parenteral use), in *National Formulary*, Vol. XII, p. 222 (which describes an aqueous solution of the thermostable fraction of mammalian liver) or in *National Formulary*, Vol. XI, p. 192-94 (which describes several thermostable liver preparations). Alternatively, the starting material may be fresh liver, frozen liver or a commercially-available liver preparation.

An acetone-insoluble fraction is separated from the starting material. This may be accomplished by admixing a large excess of acetone with the starting material which results in an acetone-insoluble fraction that is separated from the acetone. The treatment with acetone may be repeated. The acetone-insoluble fraction, after being separated from the acetone, is dissolved in water. Any remaining acetone is removed by, for example, distillation. The material effective in treating Epstein-Bart virus infection is contained in the water solution.

Alternatively, and preferably, before the acetone extraction, the starting material is dissolved in water with phenol. The solution is incubated at room temperature and after incubation, the solution is clarified by filtration, and the solution is passed over a cation exchange resin. The resulting resin-treated solution is then concentrated by evaporation, diluted with water, and centrifuged. The acetone-insoluble fraction is then separated from the supernatant by adding a large excess of acetone and further processed as described above.

The acetone-insoluble fraction may be further purified to remove the color pigments by treatment with activated charcoal. For example, the acetone-insoluble fraction may be dissolved in water and contacted with ammonia-activated charcoal.

A pharmaceutically-acceptable preservative usually is added to the water solution. For instance, phenol at from about 0.05 to about 1%, preferably about 0.5% may be added.

The liver extract useful in the present invention may be prepared according to the following examples.

Example 1 Preparation of Liver Extract

Liver Fraction I, described in National Formulary XI, page 193, was dissolved in water to a concentration of 16% by weight. Phenol was added to a final concentration of 1%. The solution was mixed and incubated for seven days at room temperature. It was then clarified by filtration, and diluted to 8% solids by weight in water.

This aqueous solution was then passed three times through a cation exchange resin (sulfonated polystyrene). The resin-treated solution was clarified by filtration and concentrated to 40% total solids by weight by evaporation under vacuum at 65°–70° C. Cold water (5°–10° C.) was added (five volumes of water to seven volumes of liver solution) with mixing. The resultant solution was then centrifuged and the supernatant collected (Sharples-type centrifuge at 1 liter per minute). Phenol was added to a final concentration 0.5–1%.

The solution was adjusted to pH 6.0–7.0, with HCl or NaOH as necessary, clarified by filtration, and heated to 40° C. Then acetone was added (20–30 liters acetone per liter liver solution). The acetone-precipitable material was allowed to settle and most of the acetone was decanted off. The remaining suspension was incubated overnight at room temperature, after which the suspension was diluted to 10 liters with water, and the acetone was removed by distillation. Phenol and water were then added to give a final preparation containing 0.5% phenol and greater than 25 mg total solids per ml (herein designated "KU 10,000").

KU 10,000 was adjusted to pH 6.0–7.0 with HCl or NaOH, as necessary and diluted to 25 mg total solids per ml. with water (i.e., 2.5% by weight solids). The solution was then sterile filtered in suitable vials for use. This final solution is referred to herein as "KU 10,001".

Example II—Physically Active Polypeptide Separation

A large excess of acetone "1800 ml" was added to eight vials KU 10,001 prepared according to Example I, 20 ml/vial, total of 160 ml, and left to stand at room temperature for four hours. After the precipitate settle down at the bottom of the beaker, the clear acetone layer decanted and the remaining suspension centrifuged for five minutes at 3000 RPM. The pellet then dissolved in 160 ml of water and freeze dried to produce about 4.0 g of dry powder consists of 0.3 mg protein/1 mg of dry powder weight. These samples were designated KU 10,172, KU 10,185, KU 10,211, KU 10,244 and KU 10,275.

One gram of the dry powder was taken in 7 ml of 50 mM phosphate buffer, pH 7.5 and passed through a 100×2.5 cm column packed with Sephadex G50 suitable for use as a molecular sieve that exclude (does not retard) molecules with a molecular weight greater than 30,000 or BIOGEL p10 which exclude molecules with a molecular weight greater than 20,000. The column was equilibrated with 50 mM phosphate buffer before use at flow rate of 36 ml/hr. The column was eluted with 50 mM phosphate buffer pH 7.5. Seven ml. fractions were collected, and read at A280. Fractions were tested for angiotensin converting enzyme inhibition (using Furylacryloylphenylalanylglycylglycine as substrate) as described by Bush, Henry and Slasarchyk; *J. of Antibiotics* 37(4), 330 (1984). All fractions eluted before angiotensin converting enzyme inhibition were pooled according to the following table.

| Loaded KU # | KU # | Pool # | Tube # |
| --- | --- | --- | --- |
| 10,244 | 10,245 | 1 | 22-30 |
|  | 10,246 | 2 | 31-50 |
| 10,185 | 10,190 | 1 | 14-16 |
|  | 10,191 | 2 | 18-20 |
|  | 10,192 | 3 | 21-23 |
|  | 10,193 | 4 | 26-29 |
| 10,275 | 10,275-I | 1 | 35-46 |
|  | 10,275-II | 2 | 47-58 |
|  | 10,275-III | 3 | 59-68 |

All pooled samples were concentrated, dialyzed in cellulose dialysis tubing with a molecular weight cut off of 1,000 and lyophilized.

Example III—Physically Active Polypeptide Separation

KU 10,172 prepared according to Example II was fractionated on reverse phase $C_{18}$ prep column, eluted with buffer A: 20 mM ammonium acetate pH 7.0, B: 80% acetonitrite in buffer A, gradient run at 214 nm, programmed zero to 80% B in 80 min. at 8.4 ml/min. Fractions collected 8.4 ml/test tube. All tubes were analyzed by analytical $C_{18}$ reverse phase column and size exclusion high pressure liquid chromatography column Tsk 125 and pooled to twelve fractions based on its retention times. Eight fractions KU 10,201 to KU 10,208 were tested for anti-viral activity and showed a significant cell protection activity.

Example IV—Further Purification of Physically Active Polypeptide

KU 10,203 and KU 10,207 prepared according to Example III were further purified on reverse phase $C_{18}$ prep column, eluted with buffer A: 20 mM ammonium actuate pH 7.0, B: 80% acetonitrile in buffer A, gradient run at 214 nm, programmed: Zero to 80% B in 80 min, at 8.4 ml/min. Fractions collected 8.4 ml test tube. All tubes were analyzed by analytical $C_{18}$ reverse phase column and size exclusion high pressure liquid chromatography column (Tsk 125) and pooled according to its retention times to produce KU 10,214 and KU,215. The cDNA from rat liver for the KU 10,214 and KU 10,215 fractions that were active in the bioassay was isolated and cloned using the polymerase chain reaction technique. The desired sequence to be amplified was that of the gene in pig liver cells that encodes the peptides in the KU 10,214 and KU 10,215 fractions.

Active Fraction Peptide Amino Terminal Amino Acid Sequencing

Ten amino acids of amino terminal sequence of KU 10,214 and KU 10,215 were determined by Edman degradation using an Applied Biosystems model 477A automated peptide sequencer with attached High Pressure Liquid Chromatography model 120A on-line phenyl isothiocyanate analyzer found to be (Ala or Val or Ile) Glu (His or Pro) Gly (Tyr or Met or Thr) His Gly Pro His Gly. More specifically, KU 10,214 has the amino acid sequence: (Ala or Val or Ile) - (Glu or Gln) - (His or Pro or Arg) - Gly - Thr - His - X - Pro - His - Gly KU 10,215 has the amino acid sequence: (Ala or Val or Ile) - (Glu or Gln) - (His or Pro) - Gly - (Tyr or Met) - His - Gly - X - His - Gly - X - X - Gly - X - Gln Due to the similarity of both sequences, we proposed a sequence to be used for our Polymerase Chain Reaction (PCR) work using the following deca peptide sequence. Ala - Glu - His - Gly - Tyr - His - Gly - Pro - His - Gly.

Polymerase Chain Reaction Primer Design

The oligonucleotide primer 5'CATGGICCICATG-GI3' [I indicates Inosine] was designed based on the five amino acid sequence (HGPHG) region sequence that was common to both the KU 10,214 and KU 10,215 fractions active in the bioassay. This primer corresponds to the indicated amino acids regardless of codon usage except for His. Codon bias analysis for all pig gene sequences found in the databank Genbank 66 showed His codon at CAT to be used about 2.5 time as often as His codon CAC. This and the rarity of CG dinucleotides in peptide coding regions of mammalian genomes (Sambrook, J., Fritsch, E. F. and Maniatis, T. (1989) in "Molecular Cloning: A Laboratory Manual", 2nd edition, Cold Spring Harbor Laboratory, Cold Spring Harbor, N.Y.) dictated use of CAT and not CAC for His in this sequence producing a primer sequence of 5'CATGGICCICATGGI 3'. This primer was prepared by conventional techniques using an Applied Biosystems DNA synthesizer. See FIG. 1.

RNA Isolation

Total RNA (2.5 mg) was isolated from 1.5 grams of fresh liver tissue from a female pig by rapid homogenation in guanidine thiocyanate followed by extraction with phenol (Chomczynski, P. and Sacchi, N. (1987) Anal. Biochem 162, 156–159). After two successive precipitations with isopropanol, the purified RNA was dissolved in water. The RNA was then subjected to poly(U) Sepharose chromatography, (Jacobson, A. (1987) Meth. Enzymology 152, 254–261), which yielded 21 μg of Poly(A)+RNA from 1 mg of total RNA.

cDNA Synthesis and Intermediate Polymerase Chain Reaction Amplification

Double stranded cDNA was prepared from the Poly-(A)+RNA by a modification of the method of Gubler and Hoffman (Gene 25, 283 (1983)). Five μg of Poly-(A)+RNA was used with an oligo(dT)-Hind III primer and AMV reverse transcriptase to synthesize the first strand, and second strand conversion was accomplished using RNase H and E. Coli DNA polymerase I. The yield was 30% first strand conversion and 100% second strand conversion. The double stranded cDNA was extracted with phenol and precipitated with ethanol by conventional methods. After treatment with T4 DNA polymerase to flush the ends, the cDNA was ligated with UNIAMP adaptors (Clontech Labs Inc. 800-662-CLON) under conditions described by the manufacturer. Following ligation, 3 μl of a 1:10 diluation of the cDNA was amplified by polymerase chain reaction in the Perkin Elmer Cetus GENEAMP System using a single UNIAMP primer (Clontech) under conditions described by the manufacturer. A sample of the reaction products was analyzed by agarose gel electrophoresis in the presence of ethidium bromide. The results showed a distribution of cDNA products that closely matched the pattern of unamplified cDNA. The remainder of the reaction products were purified by extraction with phenol and SEPHAROSE (Pharmacia Co.) CL-4B chromatography. These intermediate amplification and purification steps produced a sufficient amount of pure cDNA free of extraneous sequences which could have interfered with subsequent procedures.

Polymerase Chain Reaction Amplification with the Specific Primer

The amplified cDNA was precipitated with ethanol, collected by centrifugation and dissolved in 20 μl water. A 1 μl sample was used for polymerase chain reaction amplification with the specific primer described above in combination with oligo (dT)-Hind III primer. Conditions for polymerase chain reaction were 30 cycles at 94° C. for 1 minute, and 72° C. for 2 minutes per cycle, with a final extension at 72° C. for 5 minutes. A fraction of the reaction products were analyzed by agarose gel electrophoresis in the presence of ethidium bromide. The results showed 3 major DNA species in the range of 200 bp (base pairs), 400 bp and 500 bp. Control reactions in which the primers were omitted produced no detectable products. The strategy for sequencing this DNA is shown in FIGS. *2a*, *2b*, *2c* and *2d*.

Cloning of the Polymerase Chain Reaction Products

The remainder of the polymerase chain reaction products was treated with T4 DNA polymerase to flush the ends, and then purified by phenol extraction and ethanol precipitation. The DNA was ligated with ECOR I linkers under standard conditions. Following digestion with ECO RI and Hind III and removal of small molecules by SEPHAROSE (Pharmacia Co.) CL-4B chromatography, the prepared DNA was ligated with ECO RI/Hind III EXLOX vector arms, packaged in vitro, and plated on *E. Coli* by standard methods. The resulting library contained $3\times10^5$ independent clones and was amplified to a titer of $3\times10^{10}$ pfμ/ml.

Verification of cloning

The library was plated at a density corresponding to approximately 1,000 plaques per 82 mm plate. Plaque lifts were prepared and hybridized with random-primer labeled DNA probes by conventional methods. Using a probe from DNA amplified with the specific primer described above, virtually every plaque produced a positive hybridization signal. This indicated the library contained the desired inserts of polymerase chain reaction products.

DNA sequencing

Six randomly chosen plaques were converted to plasmid subclones for DNA sequence analysis. Restriction enzyme analysis showed an insert of approximately 500 bp in four of these isolates. Plasmid DNA was prepared and sequenced directly using T7 DNA polymerase (promega) and chain-terminating dideoxynucleotides (Mierendorf, R. C. and Pfeffer, D. (1987) Meth. Enzymol. 152, 556–562).

DNA Sequencing

Sequencing experiments determined 96 base pairs at the 5' end and 110 pairs at the 3' of the cDNA insert, which appeared to be identical in the clones sequenced.

The 5' 96 base pairs encoded a 32 amino acid polypeptide (Sequence Id. No. 1) whose first four amino acids GPHG corresponded to those of the primer HPGHG. (Sequence Id. No. 2) The 110 pairs at the 3' end (Sequence Id. No. 3) had a TAA or ATG stop codon in all three reading frames, so the C-terminal of the polypeptide is L (encoded by 5'CTA3'), (Sequence Id. No. 4 which has 8 amino acids and is encoded by (Sequence Id. No. 5) and/or (Sequence Id. No. 6) which has 21 amino acids and is encoded by Sequence Id. No. 7. As such the polypeptides are characterized by the Sequence Id. No. 1 at the 5' end and Sequence Id. Nos. 4 and 6.

Example V Physical and Chemical Tests on Physiologically Active Polypeptide

Thus, the physiologically-active polypeptide may be characterized by its physical and chemical properties. The active polypeptide is insoluble in acetone, and soluble in water. It has a molecular weight as determined by molecular sieve chromatography experiments to be about 5,000–40,000.

ADMINISTRATION OF POLYPEPTIDES

The polypeptides useful in the present invention preferably are administered by injection, for example, intramuscular injection. However, other forms of administration are contemplated. The polypeptides may be employed in the form of pharmaceutically-acceptable salts of the components, such as the alkali metal salts. The pharmaceutically-acceptable amides, lower alkyl esters, protected derivatives, other derivatives and analogues of the components of the polypeptides are also contemplated.

Although, as indicated, the polypeptides may be used as a water solution, it may also be utilized in association with other pharmaceutical carriers, for example, in saline solution. In any case, since the polypeptide is preferably administered by injection, it is contemplated that the extract will be contained in a water base carrier. A preferred product is a polypeptide water solution containing about 2.5% by weight of polypeptide. More generally, the polypeptide ranges from 5 µg to 500 µg per ml of carrier.

ADMINISTRATION OF LIVER EXTRACT

The acetone-insoluble liver extract useful in the present invention preferably is administered by injection, for example, intramuscular injection. However, other forms of administration are contemplated.

The liver extract may be employed in the form of pharmaceutically-acceptable salts of the components, such as the alkali metal salts. The pharmaceutically-acceptable amides, lower alkyl esters, protected derivatives, other derivatives and analogues of the components of the liver extract are also contemplated.

Although, as indicated, the liver extract may be used as a water solution, it may also be utilized in association with other pharmaceutical carriers, for example, in saline solution. In any case, since the liver extract is preferably administered by injection, it is contemplated that the extract will be contained in a water base carrier. A preferred product is a water solution containing about 2.5% by weight of liver extract solids.

Dosages may vary depending upon the condition of the patient. Generally, however, it has been found that the administration of 2 cc. of KU 10,001 prepared as described in Example 1 intramuscularly 2 cc will produce beneficial results in as little as about 3 days.

Example 1—Assay for Early Antigen Production—Superinfection of Raji Cells (Ellen strain) with P3HR-1

A physically active polypeptide was prepared as shown in Example II. This polypeptide was tested for anti-EBV activity as follows:

Screening and Confirmation Assays for Epstein-Barr Virus

1. Virus

There are two prototypes of infectious Epstein-Barr virus. One is exemplified by the virus derived from supernatant fluids of the P3HR-1 cell line. This cell line produces nontransforming virus that causes the production of early antigen (EA) after primary infection or superinfection of B cell lines. The other prototype is exemplified by the B-95-8 virus. This virus immortalized cord blood lymphocytes and induced tumors in marmosets. It does not, however, induce an abortive productive infection even in cell lines harboring Epstein-Bart virus genome copies. The virus used in our assays is P3HR-1.

2. Cell Lines

Ramos is an exceptional B cell line derived from Burkitt's lymphoma tumor but containing no detectable Epstein-Barr virus genome copies and is EBNA negative. Ramos/AW was obtained by in vitro infection of Ramos with the P3HR-1 virus and contains one resident Epstein-Barr virus genome copy/cell. Raji is a Burkitt's lymphoma cell line containing 60 Epstein-Barr virus genomes/cell, and is the primary cell we used for screening antiviral activity against Epstein-Barr virus EA expression. Daudi is a low level producer that contains 152 Epstein-Barr virus genome copies/cell. It spontaneously expresses Epstein-Bart virus EA in 0.25%–0.5% of the cells. It was used in follow-up studies to confirm activity. These cell lines respond to superinfection by Epstein-Barr virus by expressing viral proteins EA(D) (diffuse pattern early antigen), EA(R) (restricted pattern early antigen), and VCA (viral capsid antigen). Expression of these viral proteins is measured with immunofluorescent assay using monoclonal antibodies to the different EA components and VCA. All cell lines are maintained in RPMI-1640 medium supplemented by 10% FCS, L-glutamine and 100 ug/ml gentamicin. The cultures are fed twice weekly and the cell concentration adjusted to $3 \times 10^5$/ml. The cells are kept at 37° C. in an humidified atmosphere with 5% $CO_2$.

EBV (Raji Cells).

TABLE 2

Immunofluorescence-MCG/ML
$EC_{50}$ 1.5 $IC_{50}$ >100 SI >66.7 ACV RC50 2.0

$EC_{50}$ (50% effective concentration) is the concentration required to inhibit viral cytopathogenicity by 50%.
$IC_{50}$ (50% inhibitory concentration) is the concentration required to inhibit cell proliferation by 50%.
Selective Index (S.I.) = $IC_{50}/EC_{50}$ This in vitro testing showed that the physiologically active peptide (1.5 µg/ml) blocked 50% of Epstein-Barr virus early antigen induction in Raji cells by P3HR-1 infection while 2 µg/ml of acyclovir was required to produce a similar result. The physiologically active peptide also blocked the expression of EBV's EA(D), EA(R), and VCA in the Daudi cell line thus again demonstrating significant in vitro anti-viral activity.

Example 2 - Treatment of Epstein-Barr Virus with KUTAPRESSIN (Kremers-Urban Co.)

126 of 160 (79%) patients having a syndrome of chronic fatigue for at least four months associated with Epstein-Bart virus reactivation including significantly elevated EBV-early antigen IgG titers=1:80 showed significant or marked clinical improvement with treatment with KUTAPRESSIN (Kremers-Urban Company), a porcine liver extract, 2 cc. intramuscularly daily for 10 days followed by three times a week for an average of 33 injections. KUTAPRESSIN (Kremers-Urban Company) had been used in patients in the United States in 2 cc. IM injections for indications including herpes zoster (shingles) since 1940 without reports of significant toxicity [PDR].

Example 3 - Treatment of Acute Infectious Mononucleosis

Ten patients having acute infectious mononucleosis were treated with KUTAPRESSIN (Kremers-Urban Co.). All patients presented to the doctor with the clinical findings of infectious mononucleosis and a positive EBNA IgM or monospot test establishing the diagnosis of acute infectious mononucleosis. The patients received 2 cc. of KUTAPRESSIN (Kremers-Urban Company) daily. Table 3 provides data relating to these patients.

TABLE 3

| Days of Primary Illness | Monotest | Days to Recovery |
| --- | --- | --- |
| 30 | EBNA-Igm positive | 19 |
| 14 | Elsewh positive | 20 |
| 4 | Elsewh positive | 20 |
| 60 | Elsewh positive | 15 |
| 60 | EBNA-Igm positive | 16 |
| 9 | Elsewh positive | 21 |
| 6 | Elsewh positive | 15 |
| 30 | Elsewh positive | 14 |

TABLE 3-continued

| Days of Primary Illness | Monotest | Days to Recovery |
| --- | --- | --- |
| 7 | EBNA-Igm positive | 9 |
| 7 | EBNA-Igm positive | 11 |

The length of the patient's recovery time was compared to similar patients who did not receive KUTAPRESSIN (Kremers-Urban Company) treatment. See Table 4.

TABLE 4

| Days of Primary Illness | Monotest | Days to Recovery |
| --- | --- | --- |
| 8 | EBNA-Igm positive | 20 |
| 10 | EBNA-Igm positive | 20 |
| 10 | EBNA-Igm positive | 24 |
| 8 | EBNA-Igm positive | 90 |
| 12 | EBNA-Igm positive | 120 |
| 24 | EBNA-Igm positive | 90 |
| 7 | EBNA-Igm positive | 28 |
| 7 | EBNA-Igm positive | 14 |
| 8 | EBNA-Igm positive | 30 |

Figure 4:
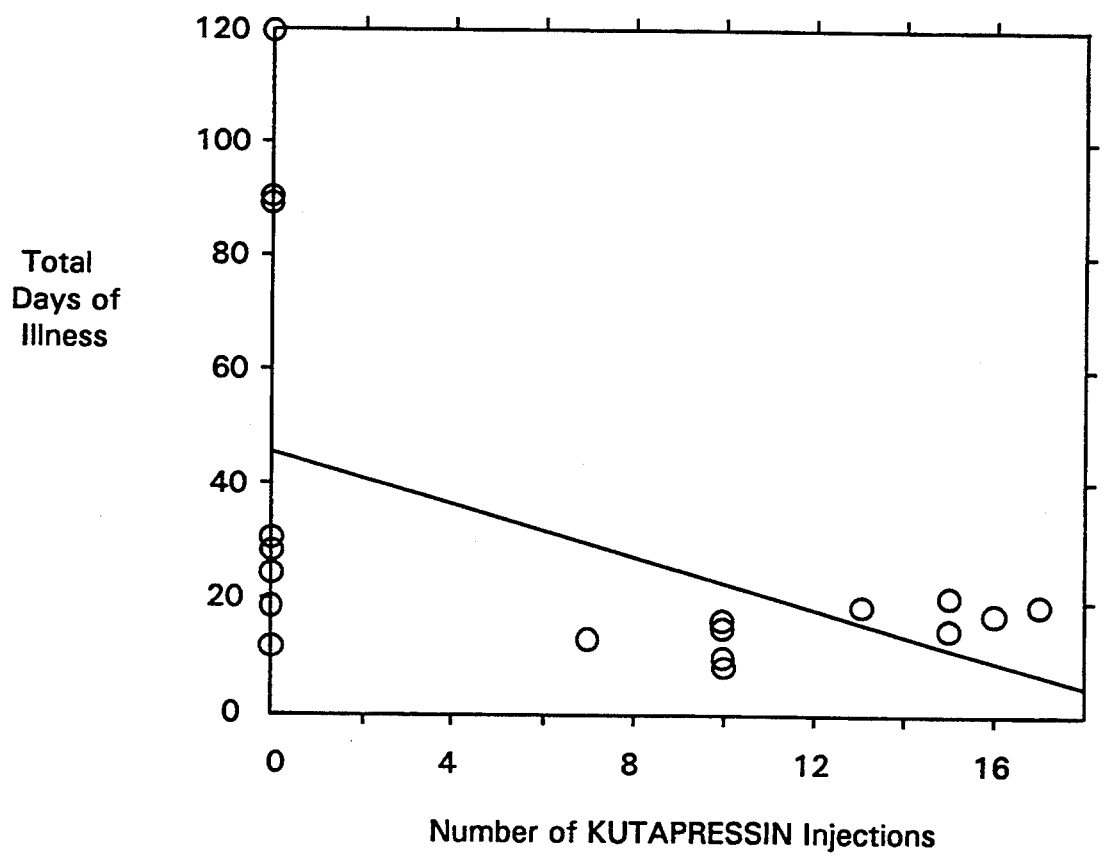
FIG. 4 shows a linear regression analysis of 19 patients as duration of illness number of days from first doctor visit to recovery=45.7-2.24 [number of KUTAPRESSIN (Kremers-Urban) injections] R=0.48.

The striking aspect of the data is that three of the nine untreaded infectious mononucleosis patients had a prolonged illness of over three months. The treated patients all recovered within three weeks of beginning KUTAPRESSIN (Kremers-Urban Company) treatment and none had such prolonged illness. See FIG. 3. A linear regression calculation on all 19 patients of total days of illness as the Y variable and number of KUTAPRESSIN (Kremers-Urban Company) injections as the X variable gives a result of: Y=45.7−2.24 X R=0.48 or [duration of illness in number of days]=45.7-2.24 [number of KUTAPRESSIN injections]. See FIG. 4.

Thus, KUTAPRESSIN (Kremers-Urban Company) injections shortened the duration of illness when used to treat infectious mononucleosis.

The treated patients did not have complications that sometimes occur during infectious mononucleosis. Four of the nine untreated patients had complications that sometimes occur during infectious mononucleosis:

1) anemia with Hemoglobin=6.2 gram %
2) otitis media
3) low TSH with hypothyroidism requiring synthroid thyroid replacement medication
4) entire body rash.

Thus, KUTAPRESSIN (Kremers-Urban Company) injections prevented complications when used to treat infectious mononucleosis.

Although the invention has been described primarily in connection with special and preferred embodiments, it will be understood that it is capable of modification without departing from the scope of the invention. The following claims are intended to cover all variations, uses, or adaptations of the invention, following, in general, the principles thereof and including such departures from the present disclosure as come within known or customary practice in the field to which the invention pertains, or as are obvious to persons skilled in the field.

We claim:

1. A method of treating an Epstein-Barr viral infection comprising administering to a mammal having Epstein-Barr virus infection a therapeutically effective amount of a mammalian liver extract, referred to as KU10,001, the extract being heat stable, insoluble in acetone and soluble in water.

2. The method of claim 1 wherein said Epstein-Barr viral infection is acute infectious mononucleosis.

3. The method of claim 1 wherein the liver extract is contained in a pharmaceutically-acceptable carrier at a concentration of about 2.5% by weight solids.

4. The method of claim 3 wherein the liver extract is contained in water.

* * * * *